(12) United States Patent
Goodale et al.

(10) Patent No.: US 7,510,684 B2
(45) Date of Patent: Mar. 31, 2009

(54) LATCH SYSTEM AND MODIFIED BLADE DESIGN FOR THICK STOPPER-CLOSED CONTAINER SAMPLING PIERCING STATION

(75) Inventors: David L. Goodale, Yorba Linda, CA (US); Steven P. Katzmann, Yorba Linda, CA (US); William M. Robins, La Habra, CA (US)

(73) Assignee: Beckman Coulter, Inc., Fullerton, CA (US)

( * ) Notice: Subject to any disclaimer, the term of this patent is extended or adjusted under 35 U.S.C. 154(b) by 536 days.

(21) Appl. No.: 09/780,804

(22) Filed: Feb. 9, 2001

(65) Prior Publication Data
US 2002/0110491 A1    Aug. 15, 2002

(51) Int. Cl.
*B01L 3/00*      (2006.01)
*B26F 1/24*      (2006.01)

(52) U.S. Cl. ............................. 422/99; 83/30; 30/358; 73/864.41

(58) Field of Classification Search ........... 83/866–868, 83/875, 879, 30, 34; 73/863.41, 864.21–864.25; 422/100, 99; 28/115; 7/151–156; 30/92.5, 30/119, 358, 360, 443, 444, 448, 449; G01N 1/00
See application file for complete search history.

(56) References Cited

U.S. PATENT DOCUMENTS

| | | | | |
|---|---|---|---|---|
| 1,485,460 A | * | 3/1924 | Johnston | 89/154 |
| 2,452,211 A | * | 10/1948 | Rosenthal | 451/37 |
| 3,273,248 A | * | 9/1966 | Halverstadt | 33/702 |
| 3,310,990 A | * | 3/1967 | Zettel | 74/409 |
| 3,319,512 A | * | 5/1967 | Isreeli | 356/410 |
| 3,388,796 A | * | 6/1968 | Roberts | 209/604 |
| 3,598,393 A | * | 8/1971 | Mater | 269/234 |
| 3,687,632 A | * | 8/1972 | Natelson | 73/864.25 |
| 3,737,245 A | * | 6/1973 | Mater | 408/225 |
| 3,791,034 A | * | 2/1974 | Carver | 30/367 |
| 3,883,305 A | | 5/1975 | Hoskins et al. | 23/253 R |
| 4,110,875 A | | 9/1978 | Foster | 28/115 |
| 4,182,208 A | * | 1/1980 | Bruno et al. | 83/118 |
| 4,271,882 A | * | 6/1981 | Valo | 144/241 |
| 4,306,356 A | * | 12/1981 | Buscher et al. | 30/362 |
| 4,478,094 A | * | 10/1984 | Salomaa et al. | 73/863.32 |
| 4,558,868 A | * | 12/1985 | Musacchia | 473/584 |
| 4,611,579 A | * | 9/1986 | Bellhouse | 600/189 |
| 4,729,876 A | | 3/1988 | Hennessy et al. | 422/103 |
| 4,745,068 A | | 5/1988 | Godfrey et al. | 435/316 |

(Continued)

FOREIGN PATENT DOCUMENTS

DE      523569      4/1931

(Continued)

*Primary Examiner*—Jill Warden
*Assistant Examiner*—Dwayne K Handy
(74) *Attorney, Agent, or Firm*—Morrison & Foerster LLP (57) ABSTRACT

A piercing station for piercing sample container caps or thick stoppers is provided. The cap piercing station utilizes a piercing blade having a generally Z-shaped cross-section, a carriage assembly for moving the blade to pierce a cap on a container, an alignment block assembly for preventing the container from being lifted up by friction with the blade when the blade is being withdrawn from a pierced cap, and a latch assembly for latching the alignment block assembly when the blade is being withdrawn.

19 Claims, 5 Drawing Sheets

U.S. PATENT DOCUMENTS

| | | | |
|---|---|---|---|
| 4,760,939 A * | 8/1988 | Ball et al. ..................... 222/23 |
| 4,798,080 A | 1/1989 | Brungraber ...................... 73/9 |
| 4,820,497 A * | 4/1989 | Howell ........................ 422/63 |
| 4,871,682 A | 10/1989 | Mazza ......................... 436/179 |
| 4,951,512 A * | 8/1990 | Mazza et al. ............. 73/864.23 |
| 4,974,457 A * | 12/1990 | Angst et al. .............. 73/863.81 |
| 5,213,764 A * | 5/1993 | Kerr et al. ................... 422/100 |
| 5,216,926 A | 6/1993 | Lipscomb ................ 73/864.25 |
| 5,236,666 A | 8/1993 | Hulette et al. ................. 422/65 |
| 5,240,679 A * | 8/1993 | Stettler ........................ 422/67 |
| 5,367,923 A * | 11/1994 | Fabbro ....................... 81/3.09 |
| 5,413,000 A * | 5/1995 | Stark et al. .............. 73/864.23 |
| 5,433,922 A | 7/1995 | Parker et al. ................. 422/63 |
| 5,455,007 A | 10/1995 | Calvo et al. .................. 422/100 |
| 5,674,237 A * | 10/1997 | Ott ............................ 606/185 |
| 5,728,954 A | 3/1998 | Uffenheimer ............ 73/864.22 |
| 5,899,122 A * | 5/1999 | Court ........................... 81/3.2 |
| 5,935,523 A | 8/1999 | McCandless et al. ........ 422/100 |
| 5,942,694 A | 8/1999 | Robins et al. ................. 73/756 |
| 5,969,272 A | 10/1999 | Tanaka .................... 73/864.24 |
| 5,993,090 A * | 11/1999 | Straka et al. ............. 400/134.4 |
| 6,148,710 A * | 11/2000 | Pottorff ....................... 83/682 |
| 6,357,322 B1 * | 3/2002 | Dolan et al. ................. 81/3.37 |
| 6,455,006 B1 * | 9/2002 | Mukai ........................ 422/100 |
| 6,511,440 B2 * | 1/2003 | Chen .......................... 600/576 |
| 6,627,156 B1 * | 9/2003 | Goodale et al. ............... 422/99 |

FOREIGN PATENT DOCUMENTS

| | | | |
|---|---|---|---|
| DE | 20017193 | | 1/2001 |
| EP | 0747689 | * | 12/1996 |
| EP | 0884575 | | 12/1998 |
| GB | 2127795 | * | 4/1984 |
| GB | 2199813 | * | 7/1988 |
| GB | 2246341 | * | 7/1990 |
| JP | 11-285589 | * | 10/1999 |
| WO | WO 96/15062 | * | 5/1996 |
| WO | WO 98/21595 | | 5/1998 |
| WO | WO 02/01179 | | 1/2002 |

* cited by examiner

LATCH SYSTEM AND MODIFIED BLADE DESIGN FOR THICK STOPPER-CLOSED CONTAINER SAMPLING PIERCING STATION

BACKGROUND OF THE INVENTION

Area of the Art

The present invention relates generally to closed container sampling systems, such as clinical chemistry analyzers, and, more specifically, to piercing stations for a closed container sampling system.

DESCRIPTION OF THE PRIOR ART

Clinical chemistry sampling and analyzing systems often use closed containers to contain samples to be analyzed. One of the initial and necessary functions of such sampling systems is to pierce the cap or stopper on closed containers in which the samples are contained to obtain an opening on the cap or stopper for the subsequent insertion of a sampling probe. This cap piercing function is often performed by a cap piercing station of the sampling system.

In conventional sampling systems, the cap piercing station often employs piercing blades that have an X-shaped cross-section. This type of conventional piercing blade with an X-shaped cross-section appears to be able to pierce through caps or stoppers that are relatively thin. However, there are several disadvantages of this conventional type of piercing blade with an X-shaped cross-section.

One of the major disadvantages of the conventional type of a piercing blade with an X-shaped cross-section is that it is not suitable for piercing thick (i.e., approximately ⅜") caps or stoppers that are made of rubber material or the like. When inserting a sampling probe into the X-shaped cut made on the cap or stopper, the probe requires too much force to penetrate, resulting in motion errors and stalling the stepper motor drive. In addition, during withdrawal of the blades and the probe, the container tends to be lifted up together with the blades or probe and is hard to be held down.

Another disadvantage of this conventional type of a piercing blade with an X-shaped cross-section is that when a sample probe is subsequently inserted through the X-shaped cut left on the cap or stopper, the sample probe tends to re-seal the cap or stopper. This changes the pressure profile inside the sample container (depending on the amount of sample in the container) which can compromise the aspiration of the sample and the clot detection system that relies on detecting pressure variations during the aspiration cycle.

A further disadvantage of this conventional type of piercing blades with an X-shaped cross-section is that a false level sense may be produced when a probe is inserted into the container through a pierced cap or stopper. Often, container caps or stoppers are made with button-shaped silicone rubber pieces supported by metallic foil closures. While piercing blades with an X-shaped cross-section can punch through the metallic foil, they only cut the metallic foil with an X-shaped cut. When the sampling probe later passes through the cap or stopper to reach the sample, it often touches the foil and thereby triggers a capacitance shift, which produces a false level sense that causes the system to believe that the sample fluid level is reached before the sample probe really reaches the fluid level.

Therefore, it is desirable to provide a piercing station with piercing blades of a new design that can reliably pierce thick caps or stoppers made of rubber or like materials and can also overcome the disadvantages of the conventional type of piercing blades with an X-shaped cross-section.

SUMMARY OF THE INVENTION

The present invention is directed to a piercing station for a closed container sampling system, such as a clinical chemistry analyzer.

One object of the present invention is to provide a piercing station for a closed container sampling system, such as a clinical chemistry analyzer. The piercing station utilizes newly designed and constructed piercing blades that can reliably pierce thick caps or stoppers made of rubber or like materials and can also overcome the disadvantages of the conventional type of piercing blades with an X-shaped cross-section.

The cap piercing station of the present invention utilizes piercing blades having a Z-shaped cross-section, which cut a Z-shaped opening in a cap or stopper on the top of a sample container. When a sampling probe is subsequently inserted, it stretches the opening, which provides the necessary ventilation for pressure equalization. The blade design is preferably a single piece Z-shaped cross-section with three points or tips. Because the Z-shaped blade is fabricated from a single piece, it reduces the cost of blade replacement. This arrangement is easily replaceable by an operator of the cap piercing station without special tools.

The cap piercing station of the present invention also utilizes a new latch assembly for reliably holding down a stopper of a sample tube, while the piercing blade(s) are retracted from a pierced rubber stopper during the cap piercing motion. The system would prevent the sample tube (or sample rack) from being lifted up into the cap pierce mechanism, jamming the analyzer, and causing motion errors and/or remixing of the sample. Because of the incorporation of the new latch assembly, a lighter hold-down spring can be used against the top of the tube cap. The lighter spring will greatly reduce the vacuum re-introduced into the tube, and avoid the increase of the vacuum level which may be caused by using a stronger spring due to the continued downward displacement of the rubber stopper during the piercing motion, followed by the removal of the strong spring-load during blade retraction, where the vertical movement of the rubber stopper under a stronger springs also compromises the proper venting of the tube (which usually starts with some vacuum inside) through the slots in the blade(s). The lighter spring also reduces the load and torque requirements on the stepper motor, lead screw and drive belt during the blade retraction sequence.

The cap piercing station of the present invention is further designed to work with handling racks that contain different sized containers and employs a cap presence sensor for detecting whether a cap or stopper is present at the top of a container for piercing. It may also utilize a shuttle mechanism for washing the blades between each piercing operation to eliminate carry-over contamination between sample containers. In addition, it may incorporate a hydro-pneumatic lubrication and washing mechanism for lubricating and washing the blade between each piercing operation. The piercing station is also well-suited for use in an existing Closed Tube Sampling (CTS) system.

These and other objects and advantages are achieved in a piercing station that includes a piercing blade having a generally Z-shaped cross-section, a carriage assembly for moving the blade to pierce a cap on a container, and a latch assembly for latching an alignment assembly to prevent the container from being lifted up by friction with the blade when the blade is being withdrawn from a pierced cap. The piercing blade has three (3) sharpened tips for piercing a cap of a container and spreading the load applied on the blade. The latch assembly has a trigger movable between a latching position when the piercing blade is being withdrawn from a pierced cap and an unlatched position after the piercing blade has been withdrawn from the pierced cap, and a spring-biased actuator engaged with the trigger and having gear rack or saw teeth. When the trigger moves to the latching position, the actuator causes its teeth to be matingly locked with a fixed segment having complementary gear rack or saw teeth to latch the alignment assembly. When the trigger moves to the unlatched position, the actuator causes its teeth to be unlocked from the teeth of the fixed segment to unlatch the alignment assembly.

The major unique and novel features of the cap piercing station of the present invention include the design and construction of piercing blades with a Z-shaped cross-section, and the use of a latch assembly.

Such an arrangement has been found to provide a number of advantages. As explained in greater detail below, the new piercing blades with a Z-shaped cross-section are well-suited for piercing thick caps or stoppers made of rubber or like materials. A sampling probe can be easily inserted into the Z-shaped cut made on the cap or stopper, thereby reducing motion errors and avoiding stalling the stepper motor drive. The blades and probe can also be easily withdrawn without lifting up the sample containers. The opening made by the insertion of the probe also provides adequate ventilation to maintain a proper pressure profile inside the container. It also avoids the problem of a metallic foil closure, thereby eliminating any false level sense when the probe is inserted into the container through the pierced cap or stopper.

The invention is defined in its fullest scope in the appended claims and is described below in its preferred embodiments.

DESCRIPTION OF THE FIGURES

The above-mentioned and other features of this invention and the manner of obtaining them will become more apparent, and will be best understood by reference to the following description, taken in conjunction with the accompanying drawings. These drawings depict only a typical embodiment of the invention and do not therefore limit its scope. They serve to add specificity and detail, in which.

DETAILED DESCRIPTION OF THE INVENTION

The present invention provides a piercing station for a closed container sampling system, such as a clinical chemistry analyzer. The present invention incorporates many features of the piercing station disclosed in a commonly owned co-pending application Ser. No. 09/599,305 filed on Jun. 22, 2000 (hereafter "application Ser. No. 09/599,305), the detailed description of which are incorporated herein in its entirety by reference and will not be repeated.

Figure 1A:
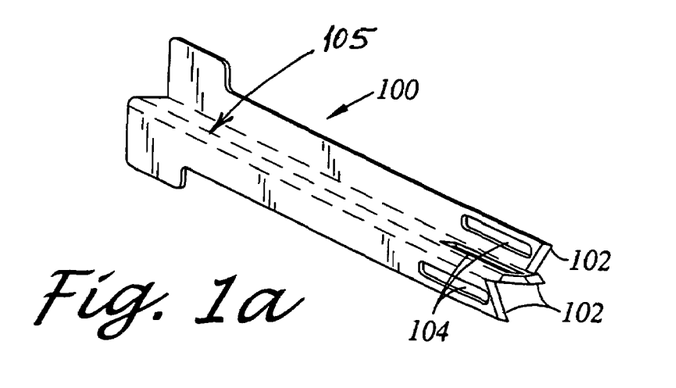
FIG. 1(a) is a perspective view of the Z-shaped blade design.
Figure 1B:
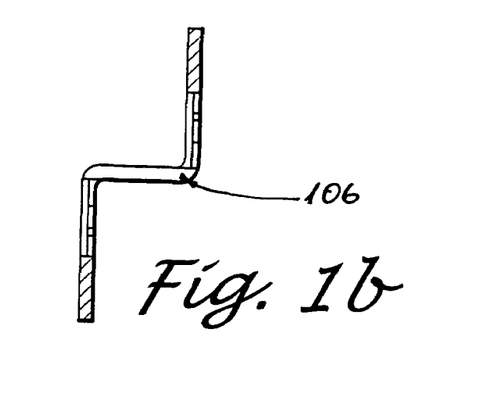
FIG. 1(b) is a cross-sectional view of the Z-shaped blade design.

Referring to FIGS. 1(a) and 1(b), there is shown the new piercing blade of the present invention 100 having a longitudinal axis 105 and a zigzagged (or Z-shaped cross-section 106 that is perpendicular to the axis 105. Preferably, the blade 100 is formed from a one thin piece of a heat-treatable stainless steel sheet. The end of the blade 100 has three (3) sharpened points or tips 102, which reduces the piercing load on the cap to minimize the stretching of the cap during piercing. As an example, the blade 100 may be made of Type 440 stainless steel hardened to Rc 58-60 and coated with titanium nitride. The hard coating such as titanium nitride on the piercing blade 100 can help to maintain the cutting points 102 of the blade 100 and increase the lubricity of the blade 100. Preferably, each blade has a thickness of 0.015". The blade may have small length-wise slots 104 at the piercing end for venting the sample tube. When a sampling probe is inserted through the opening on a thick stopper or cap made by a piercing blade, the probe will stretch the cut into an opening which provides adequate and reliable ventilation during the sample cycle, so that the obstruction detention and sample aspiration meet the system requirements.

Figure 2:
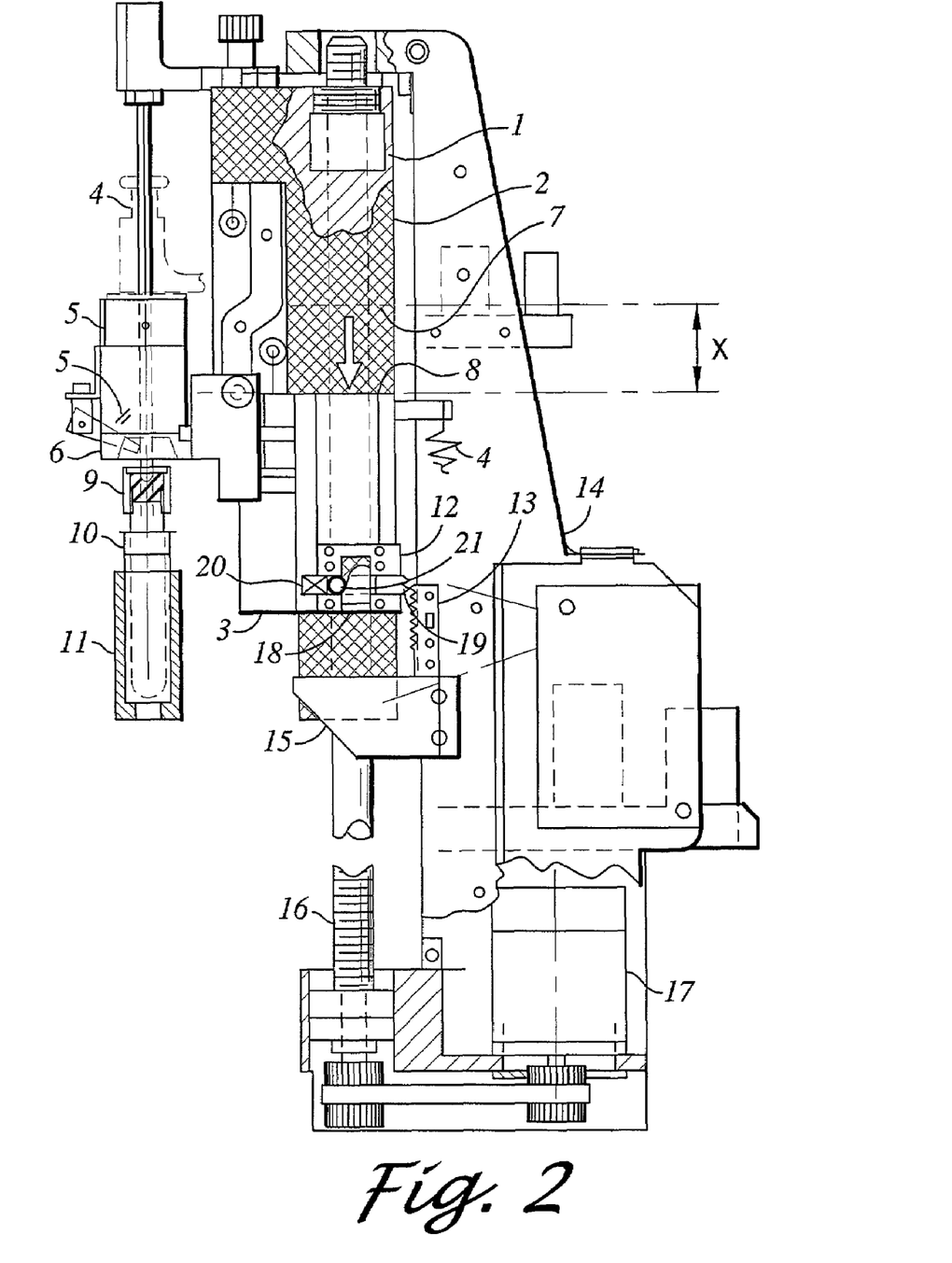
FIG. 2 is a side elevation view of a cap piercing station with its carriage assembly in a downward motion before the cap detection, showing the carriage assembly unlatched.

Referring to FIGS. 2 through 5, there is shown the present invention latch assembly 12 of a cap piercing station. The new latch assembly 12 is located on the lower left side of an alignment block 3. FIG. 2 shows that the cap piercing station is about to detect a cap 9 on the sample tube in sample rack 10, which will initiate the cap piercing cycle. As described in detail in application Ser. No. 09/599,305, the cap piercing station has a carriage assembly 2 which is driven downward from a "home" position by means of a leadnut 1 threaded into the carriage assembly 2. The leadscrew 16, threaded through leadnut 1, is driven by a stepper motor 17. Since the alignment block 3 is held in contact with the carriage assembly 2 by means of a light tension spring 4, the latch trigger 18 is forced up into the latch assembly 12, which drives the actuator slide assembly 19 toward the front of the piercer, against a compression spring 20, by means of a bearing 21. This action disengages the teeth 22 in the gear rack actuator 24 from the gear rack segment teeth 23 of gear rack segment 13. The carriage assembly 2 continues downward until the alignment arm 6 encounters the sample tube cap 9. At the cap detection point, the piercing portion of the downward stroke begins and the carriage assembly 2 separates from the alignment block 8 and the latch trigger 18 is released. The "stop" block 15 is configured so that it clears the latch trigger 18. The latch does not need to engage when the carriage is driven to this stop, since it is a fixed location, used only for priming the system.

Figure 3:
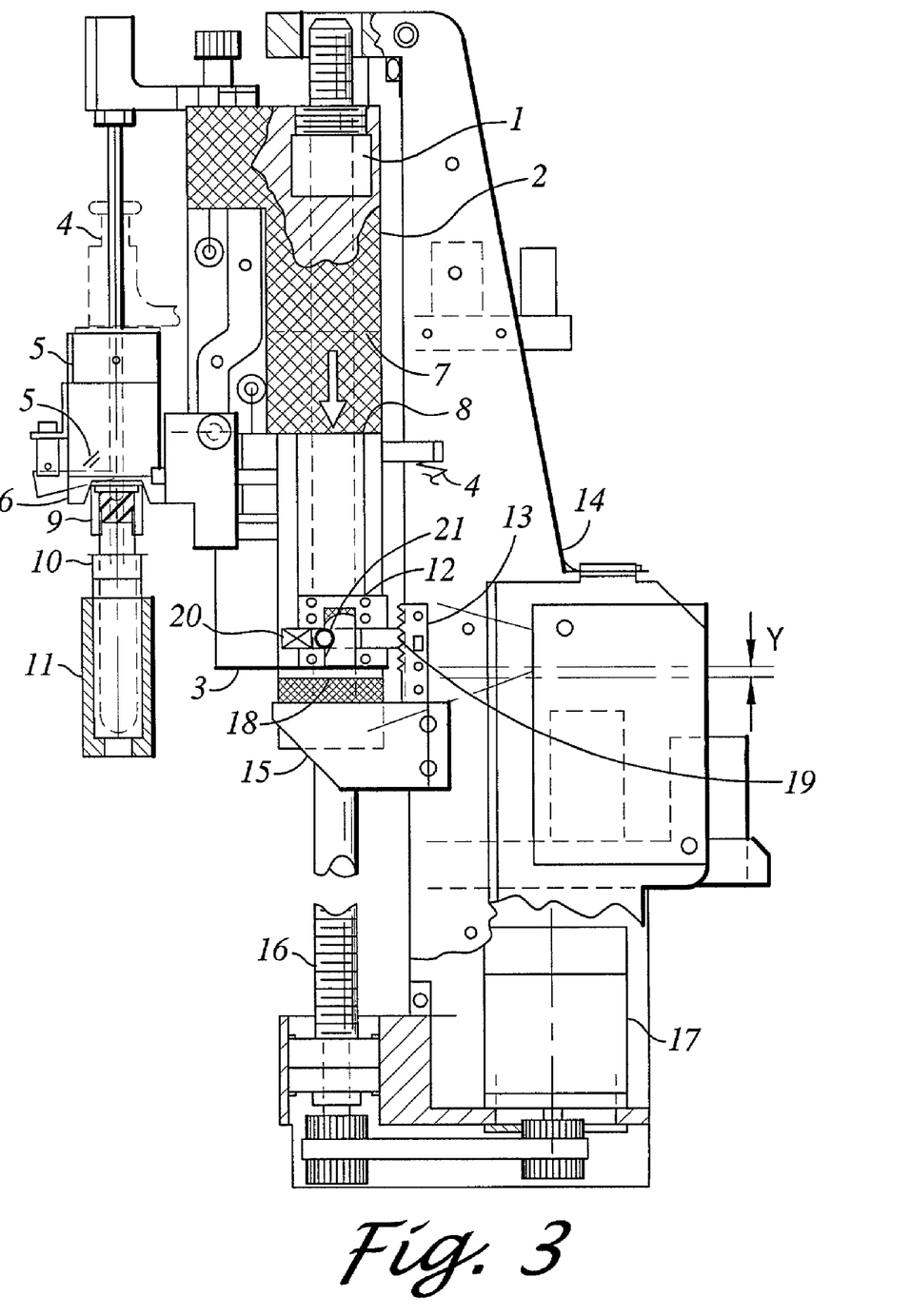
FIG. 3 is a side elevation view of a cap piercing station with its carriage assembly in a downward motion after the cap detection, showing the carriage assembly being latched.

When the alignment arm 6 makes contact with the tube cap 9 and the latch trigger 18 is released, the teeth 22 on the gear rack actuator will mesh with the gear rack segment teeth 23, due to the action of the compression spring 20. This locks the alignment block 3 in position. There is a "minimum separation" ("Y") which is the amount of over travel required by the carriage assembly 2 to fully release the trigger 18 and obtain full engagement of the teeth 22 and 23 in the "latched" position, and adequate clearance for the teeth to clear each other when "unlatched". The distance "X" between the underside 7 of the upper cross bar on the carriage assembly 2 and the top 8 of the alignment block 3 is the distance available for the cutting stroke. The cutting blade 4 is driven down through the wash tower/wick holder 5 and cuts through the tube cap 9, as more fully described in application Ser. No. 09/599,305.

At the very bottom of the cutting stroke, the leadscrew drive motor 17 is reversed and the blade assembly 4 is withdrawn from the tube and tube cap. Since the alignment block is still "latched", the tube is not lifted by the friction between the blade 4 and the cut tube cap 9. The latch remains engaged until the upward travel of the carriage and the blade causes the carriage top to contact the latch trigger and release the gear rack teeth; then the carriage and the alignment block travel up together to "home".

Figure 4:
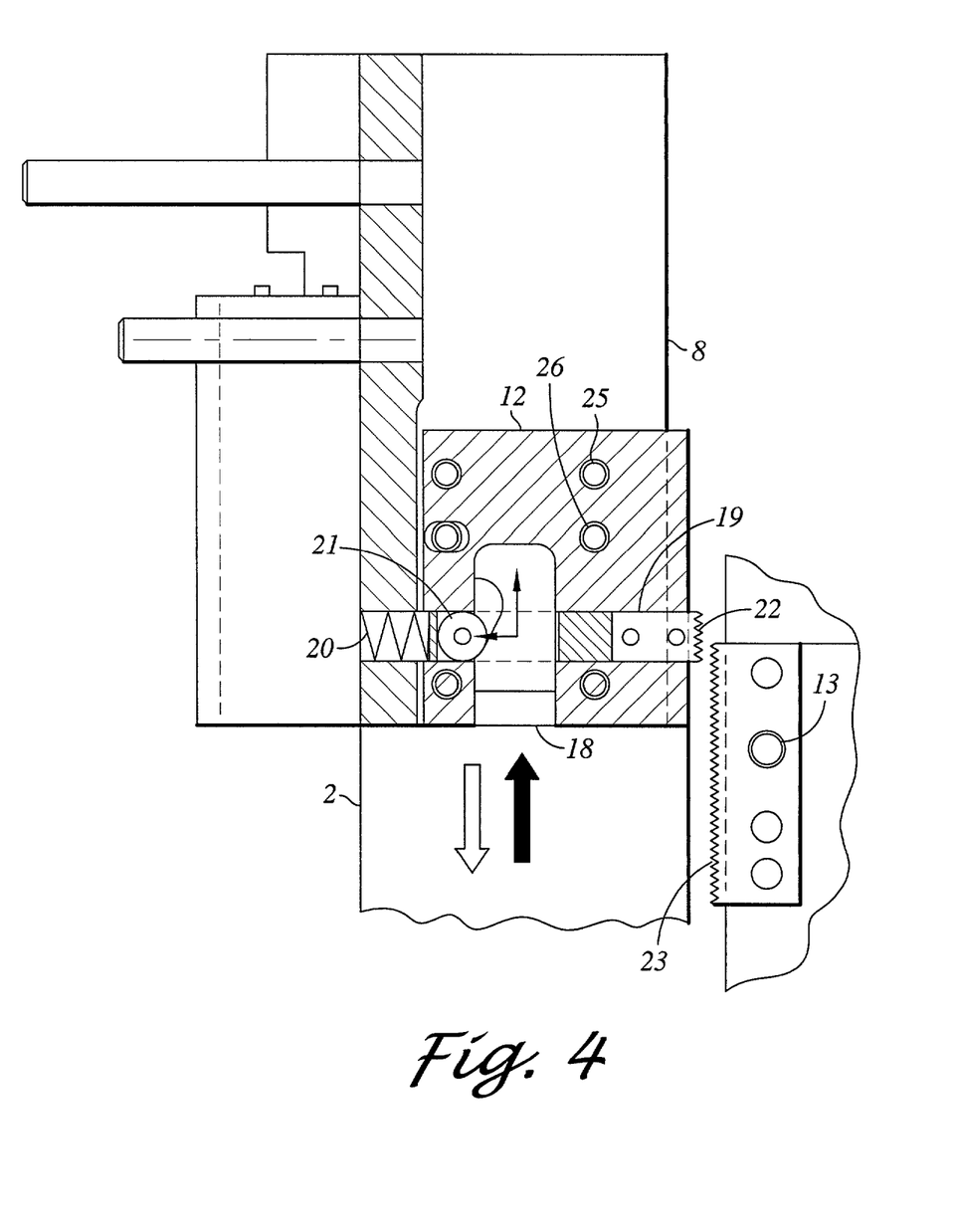
FIG. 4 is an enlarged side elevation view of the details of the latch assembly, showing the latch assembly in its retracted position.

Referring to FIG. 4, there is shown a detailed view of the latch assembly when the carriage assembly 2 is driven down prior to tube cap contact. It is also representative of the upward travel of the carriage assembly after the latch trigger 18 is lifted by contact with the carriage assembly 2. This action disengages the gear rack teeth 22 and 23. Since this occurs after the withdrawn blade clear the tube cap, there will be no disturbance to the sample tube 9 or tube rack 10.

As an example, the latch assembly 12 is attached to the alignment block by four (4) screws 25 and is pinned with two (2) dowel pins 26. Similarly, the gear rack segment 13 is attached to the frame with two (2) screws 25 and is pinned to the frame with two (2) dowel pins 26. This arrangement does not require an adjustment to the latch.

Figure 5:
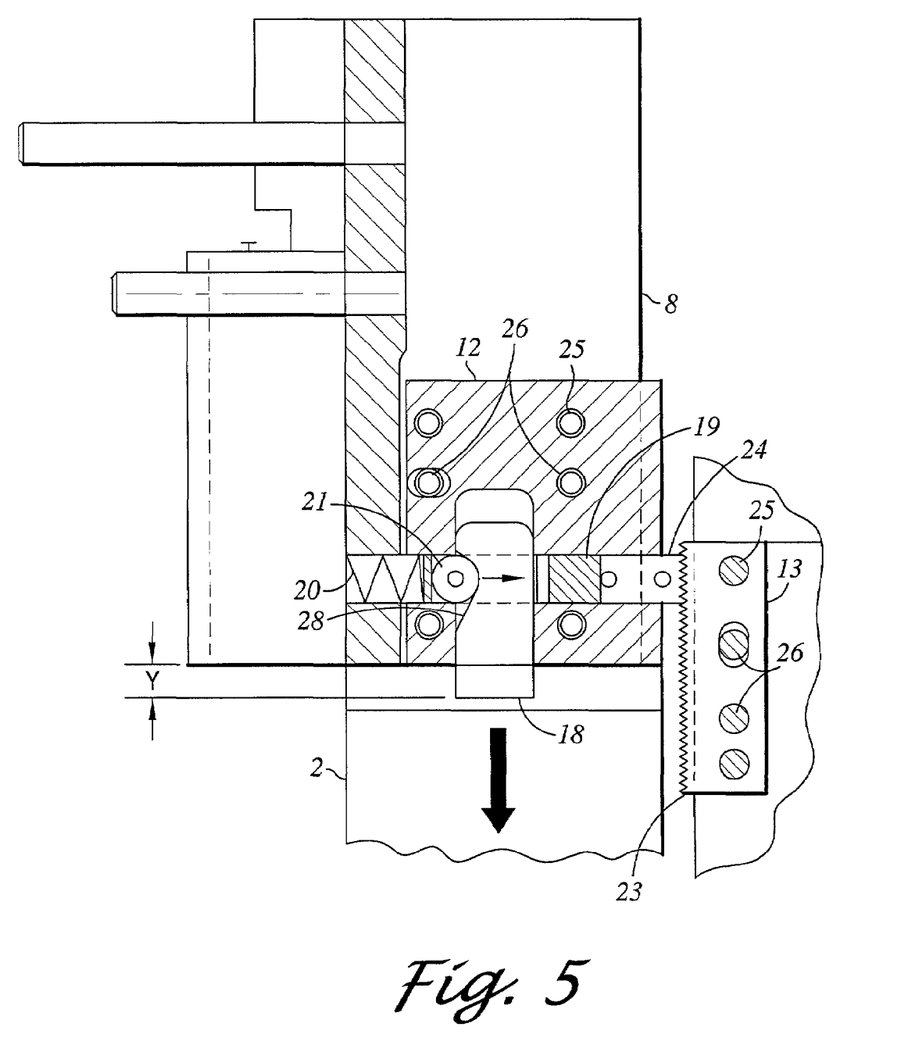
FIG. 5 is an enlarged side elevation view of the details of the latch assembly, showing the latch assembly in its engaged position.

Referring to FIG. 5, there is shown a detail view of the latch assembly 12 when the carriage assembly 2 is driven down after tube cap contact, during the cap piercing stroke. The cam surface 28 on the trigger 18 is designed so that a single spring provides both the lateral and vertical forces required to actuate the trigger 18. The gear rack teeth 22 and 23 will mesh whenever the alignment arm 6 (see FIGS. 2 and 3) contacts the tube cap during the downward travel, preventing further motion of the alignment block 3 down or up.

The alignment block assembly now uses a lighter return spring 4. Without utilizing the new latch assembly of the present invention, strong springs are required. As an example, two 20-pound springs were used without the new latch assembly, and only one 5-pound spring is used when the latch assembly is utilized, which yields a force reduction factor of 8.

Figure 6:
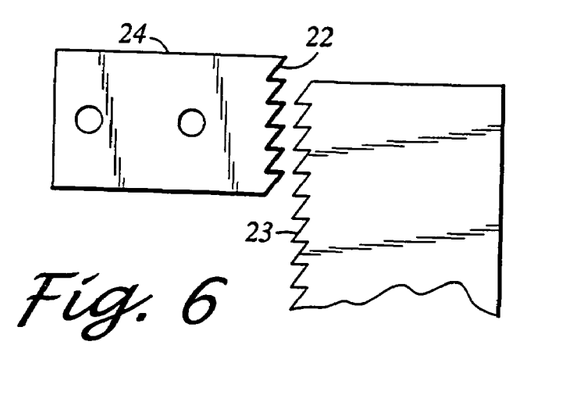
FIG. 6 is an enlarged side elevation view of an alternative "saw-tooth" design of the latch assembly.

FIG. 6 shows an alternate tooth design for a gear rack actuator and a gear rack segment. The sawtooth arrangement will prevent any inadvertent disengagement between the two parts, particularly if any lubricant gets between the teeth, which would lower the friction coefficient.

As described in more detail in application Ser. No. 09/599,305, the content of which is fully incorporated herein by reference, the piercing station of the present invention is capable of handling sample containers of various configurations or conditions held in a rack. In addition, the piercing station of the present invention may include a shuttle mechanism for cap detection. The piercing station of the present invention may also include a wash and lubrication tower for the blade and a lubrication and washing hydro-pneumatic system. The cap piercing station of the present invention has a washing system that cleans the blades between sample containers to eliminate carry-over contamination. It also has a lubrication system that lubricates the blades, which reduces force on the blades during the piercing operation and also leaves a small amount of lubricating oil on the pierced cap or stopper to reduce the force required by the sample probe to penetrate into and retract from the pierced cap or stopper later in the cycle. The oil dispenser can accurately dispense a fixed volume of oil in each cycle, without the complexity of a syringe pump that typically requires added motors and valves. The station can automatically distinguish between an "open" or a "closed" container. It also has a container height detection feature which determines whether a container is within the required range for piercing.

The piercing station of the present invention has many advantages. The new piercing blade design provides a stiff and durable piercing blade with minimum bending, which can reliably pierce a thick (i.e., typically ⅜" or thicker) rubber cap or stopper in the top of a sample tube made of either glass or plastic without leaving debris or breaking the tube. If the blade comes in contact with the sample inside the container, the blade is washed between each sample, so carry-over is minimal. The lubed piercing blade with a Z-shaped cross-section can reduce the amount of vertical force required to pierce a thick cap or stopper, which prevents jamming the cap or stopper into the sample container, and also reduces the retraction force required to strip the cap or stopper from the piercing blades. The Z-shaped cut made by the new blades allows adequate ventilation during sample probe entry, so that obstruction detection and sample aspiration meet the system requirements. Additional vertical slots in the cross blades help to vent the tube at the piercing station. The cut made in the cap or stopper also allows multiple penetrations of the sampling probe without dislodging pieces of rubber or creating excessive debris.

The Z-shaped cut pattern made by the present invention Z-shaped blade vents better for improved clot detection and sample aspiration. The Z-shaped blade also cuts through the tube caps more easily and with less stretching of the elastomer, resulting in more consistent cut size and better venting.

The mechanical latch assembly provides reliability and consistency for the cap piercing cycles without utilizing or modifying any electronic components. It also provides more reliable obstruction detection and fewer motion errors. It further allows the piercing station to handle sample tubes that are more sensitive to high spring loads. As discussed earlier, utilizing the latch assembly allows the using of a lighter spring instead of a strong spring, which in turn reduces the torque loading requirements on the motor and leadscrew combination. This also reduces the chance that the caps are pushed into the sample tubes and/or the risk that sample tubes may be broken by a high spring load. This further reduces false obstruction detection which may be triggered by a heavy spring force. In addition, this new arrangement of a light spring with the latch assembly overcomes a problem caused by a heavy spring load that often squeezes the rubber tube cap to the point that the volume in the tube is reduced, which squeezes out even more air from inside the tube through the partially vented blades during cutting, such that during extraction of the blades from the tube cap, the vacuum actually increases inside the tube after the heavy hold down springs are released and the rubber returns to its original dimensions.

The set up and installation of the new piercing station is also safe and easy. The piercing station of the present invention is interchangeable with an existing CTS system.

The foregoing is meant to illustrate, but not to limit, the scope of the invention. Indeed, those of ordinary skill in the art can readily envision and produce further embodiments, based on the teachings herein, without undue experimentation.

It is to be understood that the form of the system depicted in FIGS. 1 through 6 has been chosen only for the purpose of describing a particular embodiment and function of the invention, and that the arrangement of the invention can be addressed in various ways and incorporated in other types of devices, all of which will be evident to those working in the art.

It is to be understood that the particular arrangement of the piercing station of the present invention may vary, depending on the sampling system incorporated or working together with, but that the determination of necessary variation is well within the skill of the art in view of the instant disclosure.

Suitable components that are commercially available would be known to those of ordinary skill in the art in view of this disclosure. It is to be further understood that any comparable means of accomplishing this goal is within the scope of this invention.

The present invention may be embodied in other specific forms without departing from its essential characteristics. The described embodiment is to be considered in all respects only as illustrative and not as restrictive. The scope of the invention is, therefore, indicated by the appended claims rather than by the foregoing description. All changes which come within the meaning and range of the equivalence of the claims are to be embraced within their scope.

What is claimed is:

1. An apparatus for piercing container caps, comprising:
    a) a piercing blade having a longitudinal axis and a zig-zagged cross-section that is perpendicular to said axis;
    b) an alignment arm for moving said blade in a linear motion along said longitudinal axis to pierce a cap on a container, comprising a carriage assembly for moving said alignment arm, wherein movement of said blade is limited to linear motion along said longitudinal axis, wherein said zig-zagged cross-section produces a Z-shaped cut on said cap; and
    means for driving said carriage assembly.

2. The apparatus as defined in claim 1, wherein said piercing blade has at least one sharpened tip for piercing a cap of a container and spreading the load applied on the blade.

3. The apparatus as defined in claim 1, further comprising an alignment block assembly for restraining said container when said piercing blade is being withdrawn after piercing a cap.

4. An apparatus for piercing container caps comprising:
    a) a piercing blade having a longitudinal axis and a zig-zagged cross section that is perpendicular to said axis;
    b) an alignment arm for moving said blade in a linear motion along said longitudinal axis to pierce a cap on a container, comprising a carriage assembly for moving said alignment arm, wherein movement of said blade is limited to linear motion along said longitudinal axis;
    c) means for driving said carriage assembly;
    d) an alignment block assembly for restraining said container when said piercing blade is being withdrawn after piercing a cap; and
    e) a latch assembly for latching said alignment block assembly when said piercing blade is being withdrawn from a pierced cap to prevent said container from being moved by friction with said withdrawn blade.

5. The apparatus as defined in claim 4, wherein said latch assembly further comprising a trigger movable between a latching position when said piercing blade is being withdrawn from a pierced cap and an unlatched position after said piercing blade has been withdrawn from said pierced cap.

6. The apparatus as defined in claim 5, wherein said latch assembly further comprising an actuator engaged with said trigger, wherein the actuator has locking means, such that when said trigger moves to said latching position, said actuator causes its locking means to matingly lock with a fixed complimentary locking means to latch said alignment assembly, and when said trigger moves to said unlatched position, said actuator causes its locking means to unlock from said fixed complimentary locking means to unlatch said alignment assembly.

7. The apparatus as defined in claim 6, wherein said locking means of said actuator and said fixed complimentary locking means are gear rack teeth.

8. The apparatus as defined in claim 6, wherein said locking means of said actuator and said fixed complimentary locking means are saw teeth.

9. The apparatus as defined in claim 6, wherein said actuator is spring-biased.

10. An apparatus for piercing container caps, comprising:
    a) a piercing blade having a longitudinal axis and a zig-zagged cross-section that is perpendicular to said axis;
    b) an alignment arm for moving said blade in a linear motion along said longitudinal axis to pierce a cap on a container, wherein movement of said blade is limited to linear motion along said longitudinal axis, wherein said zig-zagged cross-section produces a Z-shaped cut on said cap; and
    c) means for preventing said container from being moved by friction with said blade when said blade is being withdrawn from a pierced cap.

11. The apparatus as defined in claim 10, wherein said piercing blade has at least one sharpened tip for piercing a cap of a container and spreading the load applied on the blade.

12. The apparatus as defined in claim 10 further comprising:
    a) a carriage assembly for moving said alignment arm; and
    b) means for driving said carriage assembly.

13. The apparatus as defined in claim 10, wherein said preventing means comprises an alignment block assembly for restraining said container when said piercing blade is being withdrawn after piercing a cap.

14. An apparatus for piercing container caps, comprising:
    a) a piercing blade having a longitudinal axis and a zig-zagged cross-section that is perpendicular to said axis;
    b) an alignment arm for moving said blade in a linear motion along said longitudinal axis to pierce a cap on a container, wherein movement of said blade is limited to linear motion along said longitudinal axis; and
    c) means for preventing said container from being moved by friction with said blade when said blade is being withdrawn from a pierced cap, wherein said preventing means further comprises a latch assembly for latching said alignment block assembly when said piercing blade is being withdrawn from a pierced cap to prevent said container being lifted up by friction with said withdrawn blade.

15. The apparatus as defined in claim 14, wherein said latch assembly further comprises a trigger movable between a latching position when said piercing blade is being withdrawn from a pierced cap and an unlatched position after said piercing blade has been withdrawn from said pierced cap.

16. The apparatus as defined in claim 15, wherein said latch assembly further comprises an actuator engaged with said trigger, wherein the actuator has locking means, such that when said trigger moves to said latching position, said actuator causes its locking means to matingly lock with a fixed complimentary locking means to latch said alignment assembly, and when said trigger moves to said unlatched position, said actuator causes its locking means to unlock from said fixed complimentary locking means to unlatch said alignment assembly.

17. The apparatus as defined in claim 16, wherein said locking means of said actuator and said fixed complimentary locking means are gear rack teeth.

18. The apparatus as defined in claim 16, wherein said locking means of said actuator and said fixed complimentary locking means are saw teeth.

19. The apparatus as defined in claim 16, wherein said actuator is spring-biased.

* * * * *